(12) United States Patent
Takahashi et al.

(10) Patent No.: US 8,828,662 B2
(45) Date of Patent: Sep. 9, 2014

(54) METHOD AND KIT FOR DETECTION OF MICROSATELLITE INSTABILITY-POSITIVE CELL

(75) Inventors: Ryosuke Takahashi, Kawagoe (JP); Keiichi Nagai, Higashiyamato (JP)

(73) Assignee: Hitachi, Ltd., Tokyo (JP)

( * ) Notice: Subject to any disclaimer, the term of this patent is extended or adjusted under 35 U.S.C. 154(b) by 1037 days.

(21) Appl. No.: 11/798,013

(22) Filed: May 9, 2007

(65) Prior Publication Data

US 2008/0118927 A1 May 22, 2008

(30) Foreign Application Priority Data

Aug. 23, 2006 (JP) ................................. 2006-226665

(51) Int. Cl.
*C12Q 1/68* (2006.01)
*C07H 21/04* (2006.01)

(52) U.S. Cl.
USPC ..................... 435/6.12; 536/24.31; 536/24.33

(58) Field of Classification Search
None
See application file for complete search history.

(56) References Cited

U.S. PATENT DOCUMENTS 7,022,472 B2    4/2006    Robbins et al.

FOREIGN PATENT DOCUMENTS

| JP | 2005-304497 | 3/2005 |
|---|---|---|
| WO | WO 00/26401 | 11/1999 |

OTHER PUBLICATIONS

Raevaara et al. Functional Significance and Clinical Phenotype of Nontruncating Mismatch Repair Variants of MLH1. Gastroenterology (2005) 129: 537-549.*
Edmonston et al. Colorectal carcinomas with high microsatellite instability: defining a distinct immunologic and molecular entity with respect to prognostic markers. Human Pathology (2000) 31(12): 1506-1514.*
Stefansson et al. Loss of hMSH2 and hMSH6 expression is frequent in sporadic endometrial carcinomas with microsatellite instability: A population-based study. Clinical Cancer Research (2002) 8: 138-143.*
Russo et al. Advatages and limitations of microarray technology in human cancer. Oncogene (2003) 22: 6497-6507.*
Cawkwell et al. Defective hMSH2/hMLH1 protein expression is seen infrequently in ulcerative colitis associated colorectal cancers. Gut (2000) 46: 367-369.*
Wu et al. Distinct clinicopathologic and genetic profiles in sporadic gastric cancer with different mutator phenotypes. Genes, Chromosomes, and Cancer (2000) 27: 403-411.*
Pagenstecher et al. Aberrant splicing in MLH1 and MLH2 due to exonic and intronic variants. Human Genetics (2006) 119: 9-22.*
Landry, Josette-Renée, et al. "Complex controls: the role of alternative promoters in mammalian genomes", Trends in Genetics, vol. 19 No. 11, Nov. 2003, pp. 640-648.
Kimura, Kouichi et al. "Diversification of transcriptional modulation: Large-scale identification and characterization of putative alternative promoters of human genes", Genome Research, vol. 16, Dec. 12, 2005, pp. 55-65.
Brinkman, Brigitta M.N., "Splice variants as cancer biomarkers", Chemical Biochemistry, vol. 37, 2004, pp. 584-594.
Lui, Bo et al. "Analysis of mismatch repair genes in hereditary non-polyposis colorectal cancer patients", Nature Medicine, vol. 2, No. 2, Feb. 1996, pp. 169-174.
Laiho, Päivi et al. "Low-Level Micorsatellite Instability in Most Colorectal Carcinomas[1]", Cancer Research 62, Feb. 15, 2002, pp. 1166-1170.
Deng, Guoren et al. "Methylation of CpG in a Small Region of the hMLH1 Promoter Invariably Correlates with the Absence of Gene Expression[1]", Cancer Research 59, May 1, 1999, pp. 2029-2033.
Sequence listing, "*Homo sapiens* cDNA clone FCBBF3013182, 5' end, mRNA sequence", XP002446099, Oct. 19, 2005, EBI Accession No. EMBL: DA499490, Database Accession No. DA499490.
Sequence listing, "*Homo sapiens* MLH1+ins1a insoform (MLH1) mRNA, complete cds, alternatively spliced", XP002446100, Jul. 11, 2006, EBI Accession No. EMBL: DQ648888, Database Accession No. DQ648888.
Genuardi, Maurizio et al. "Characterization of *MLH1* and *MSH2* alternative splicing and its relevance to molecular testing of colorectal cancer susceptibility", Hum Genet vol. 102 No. 1, Jan. 1998, pp. 15-20.
Kohonen-Corish, Maija et al. "RNA-based mutation screening in hereditary nonpolyposis colorectal cancer", Am. J. Hum. Genet vol. 59 No. 4, 1996, pp. 818-824.
Bachring J. et al., "A 'nonsense' mutation leads to aberrant splicing of hMLHI in a German hereditary non-polyposis colorectal cancer family", Familial Cancer 2006, vol. 5 No. 2, Jun. 2006, pp. 195-199.
Andrew, Susan E., et al., "An intronic polymorphism of the *hMLH1* gene contributes toward incomplete genetic testing for HNPCC", Genetic Testing Winter 2002, vol. 6 No. 4, Jan. 2002, pp. 319-322.
Clarke, Luka A. et al., "Pathological exon skipping in an HNPCC proband with *MLH1* splice acceptor site mutation", Genes, Chromosomes & Cancer, vol. 29 No. 4, Dec. 2000, pp. 367-370.

(Continued)

*Primary Examiner* — Angela M Bertagna
(74) *Attorney, Agent, or Firm* — Stephen J. Weyer; Stites & Harbison, PLLC

(57) ABSTRACT

A method for detecting an abnormal cell based on gene expression analysis, which is useful for cancer diagnosis, is provided. A gene expression analysis method, comprising: measuring the expression level of a transcript of a human MLH1 gene containing the nucleotide sequence as shown in SEQ ID NO: 1 at the 5'-terminus thereof and the expression level of a transcript of a human MLH1 gene containing the nucleotide sequence as shown in SEQ ID NO: 2 at the 5'-terminus thereof, in a biological sample; and comparing the expression levels, thereby detecting a cell positive for microsatellite instability.

3 Claims, 2 Drawing Sheets

(56) References Cited

OTHER PUBLICATIONS

Renkonen, E., "Novel splicing associations of hereditary colon cancer related DNA mismatch repair gene mutations", J Med Genet, vol. 41 No. 7, Jul. 2004, www.jmedgenet.com, p. e95-e100.

Mitchell, R.J. et al., "Mismatch Repair Genes *hMLH1* and *hMSH2* and colorectal cancer: a HuGE review," Am J Epidemiol, vol. 156 No. 10, Nov. 15, 2002, pp. 885-902.

Venables, Julian P. et al., "EASI-enrichment of alternatively spliced isoforms", Nucleic Acids Research, vol. 34, No. 15, Sep. 1, 2006, pp. E03-1-E103-4.

Extended European Search Report dated Sep. 11, 2007.

\* cited by examiner

|  | LoVo | HCT116 | RKO | SW48 | COLO320 DM | COLO201 |
|---|---|---|---|---|---|---|
| Expression | v1 < v3 | v1 < v3 | v1(-),v3(+) | v1(-),v3(+) | v1 > v3 | v1 > v3 |
| MSI | + | + | + | + | - | - |
| Methylation | - | - | + | + | - | - |

```
                               SEQUENCE LISTING

<160> NUMBER OF SEQ IDS NOS: 14

<210> SEQ ID NO 1
<211> LENGTH: 295
<212> TYPE: DNA
<213> ORGANISM: Homo sapiens

<400> SEQUENCE: 1
aagaacgtga gcacgaggca ctgaggtgat tggctgaagg cacttccgtt gagcatctag     60
acgtttcctt ggctcttctg gcgccaaaat gtcgttcgtg gcaggggtta ttcggcggct    120
ggacgagaca gtggtgaacc gcatcgcggc gggggaagtt atccagcggc cagctaatgc    180
tatcaaagag atgattgaga actgtttaga tgcaaaatcc acaagtattc aagtgattgt    240
taaagaggga ggcctgaagt tgattcagat ccaagacaat ggcaccggga tcagg         295

<210> SEQ ID NO 2
<211> LENGTH: 213
<212> TYPE: DNA
<213> ORGANISM: Homo sapiens

<400> SEQUENCE: 2
gcatgcccac aacggcggag gccgccgggt ccctgacgt gccagtcagg ccttctcctt      60
ttccgcagac cgtgtgtttc tttaccgctc tcccccgaga ccttttaagg gttgtttgga    120
gttttagatg caaaatccac aagtattcaa gtgattgtta agagggagg cctgaagttg     180 attcagatcc aagacaatgg caccgggatc agg                                 213

<210> SEQ ID NO 3
<211> LENGTH: 204
<212> TYPE: DNA
<213> ORGANISM: Homo sapiens

<400> SEQUENCE: 3
aagaacgtga gcacgaggca ctgaggtgat tggctgaagg cacttccgtt gagcatctag     60
acgtttcctt ggctcttctg gcgccaaaat gtcgttcgtg gcaggggtta ttcggcggct    120
ggacgagaca gtggtgaacc gcatcgcggc gggggaagtt atccagcggc cagctaatgc    180
tatcaaagag atgattgaga actg                                           204

<210> SEQ ID NO 4
<211> LENGTH: 122
<212> TYPE: DNA
<213> ORGANISM: Homo sapiens

<400> SEQUENCE: 4
gcatgcccac aacggcggag gccgccgggt ccctgacgt gccagtcagg ccttctcctt      60
ttccgcagac cgtgtgtttc tttaccgctc tcccccgaga ccttttaagg gttgtttgga    120
gt                                                                   122

<210> SEQ ID NO 5
<211> LENGTH: 91
<212> TYPE: DNA
<213> ORGANISM: Homo sapiens

<400> SEQUENCE: 5
tttagatgca aaatccacaa gtattcaagt gattgttaaa gagggaggcc tgaagttgat     60
tcagatccaa gacaatggca ccgggatcag g                                   91
```

```
<210> SEQ ID NO 6
<211> LENGTH: 20
<212> TYPE: DNA
<213> ORGANISM: Artificial Sequence
<220> FEATURE:
<223> OTHER INFORMATION: chemically synthesized primer

<400> SEQUENCE: 6
cagcggccag ctaatgctat                                               20

<210> SEQ ID NO 7
<211> LENGTH: 27
<212> TYPE: DNA
<213> ORGANISM: Artificial Sequence
<220> FEATURE:
<223> OTHER INFORMATION: chemically synthesized primer

<400> SEQUENCE: 7
ccattgtctt ggatctgaatc aacttc                                       27

<210> SEQ ID NO 8
<211> LENGTH: 24
<212> TYPE: DNA
<213> ORGANISM: Artificial Sequence
<220> FEATURE:
<223> OTHER INFORMATION: chemically synthesized primer

<400> SEQUENCE: 8
gggttgtttg gagttttaga tgca                                          24

<210> SEQ ID NO 9
<211> LENGTH: 33
<212> TYPE: DNA
<213> ORGANISM: Artificial Sequence
<220> FEATURE:
<223> OTHER INFORMATION: chemically synthesized probe

<400> SEQUENCE: 9
caagtattca agtgattgtt aaagagggag gcc                                33

<210> SEQ ID NO 10
<211> LENGTH: 21
<212> TYPE: DNA
<213> ORGANISM: Artificial Sequence
<220> FEATURE:
<223> OTHER INFORMATION: chemically synthesized primer

<400> SEQUENCE: 10
ctggacgaga cagtggtgaa c                                             21

<210> SEQ ID NO 11
<211> LENGTH: 26
<212> TYPE: DNA
<213> ORGANISM: Artificial Sequence
<220> FEATURE:
<223> OTHER INFORMATION: chemically synthesized primer

<400> SEQUENCE: 11
atactggcta atcctcaaa ggactg                                         26

<210> SEQ ID NO 12
<211> LENGTH: 21
<212> TYPE: DNA
<213> ORGANISM: Artificial Sequence
<220> FEATURE:
```

<223> OTHER INFORMATION: chemically synthesized primer

<400> SEQUENCE: 12
tttctttacc gctctccccc g                     21

<210> SEQ ID NO 13
<211> LENGTH: 2524
<212> TYPE: DNA
<213> ORGANISM: Homo sapiens
<220> FEATURE:
<221> NAME/KEY: CDS
<222> LOCATION: (61)..(2331)

<400> SEQUENCE: 13

```
attggctgaa ggcacttccg ttgagcatct agacgtttcc ttggctcttc tggcgccaaa      60 atg tcg ttc gtg gca ggg gtt att cgg cgg ctg gac gag aca gtg gtg      108
Met Ser Phe Val Ala Gly Val Ile Arg Arg Leu Asp Glu Thr Val Val
 1               5                  10                  15 aac cgc atc gcg gcg ggg gaa gtt atc cag cgg cca gct aat gct atc      156
Asn Arg Ile Ala Ala Gly Glu Val Ile Gln Arg Pro Ala Asn Ala Ile
             20                  25                  30 aaa gag atg att gag aac tgt tta gat gca aaa tcc aca agt att caa      204
Lys Glu Met Ile Glu Asn Cys Leu Asp Ala Lys Ser Thr Ser Ile Gln
         35                  40                  45 gtg att gtt aaa gag gga ggc ctg aag ttg att cag atc caa gac aat      252
Val Ile Val Lys Glu Gly Gly Leu Lys Leu Ile Gln Ile Gln Asp Asn
     50                  55                  60 ggc acc ggg atc agg aaa gaa gat ctg gat att gta tgt gaa agg ttc      300
Gly Thr Gly Ile Arg Lys Glu Asp Leu Asp Ile Val Cys Glu Arg Phe
 65                  70                  75                  80 act act agt aaa ctg cag tcc ttt gag gat tta gcc agt att tct acc      348
Thr Thr Ser Lys Leu Gln Ser Phe Glu Asp Leu Ala Ser Ile Ser Thr
                 85                  90                  95 tat ggc ttt cga ggt gag gct ttg gcc agc ata agc cat gtg gct cat      396
Tyr Gly Phe Arg Gly Glu Ala Leu Ala Ser Ile Ser His Val Ala His
            100                 105                 110 gtt act att aca acg aaa aca gct gat gga aag tgt gca tac aga gca      444
Val Thr Ile Thr Thr Lys Thr Ala Asp Gly Lys Cys Ala Tyr Arg Ala
        115                 120                 125 agt tac tca gat gga aaa ctg aaa gcc cct cct aaa cca tgt gct ggc      492
Ser Tyr Ser Asp Gly Lys Leu Lys Ala Pro Pro Lys Pro Cys Ala Gly
    130                 135                 140 aat caa ggg acc cag atc acg gtg gag gac ctt ttt tac aac ata gcc      540
Asn Gln Gly Thr Gln Ile Thr Val Glu Asp Leu Phe Tyr Asn Ile Ala
145                 150                 155                 160 acg agg aga aaa gct tta aaa aat cca agt gaa gaa tat ggg aaa att      588
Thr Arg Arg Lys Ala Leu Lys Asn Pro Ser Glu Glu Tyr Gly Lys Ile
                165                 170                 175 ttg gaa gtt gtt ggc agg tat tca gta cac aat gca ggc att agt ttc      636
Leu Glu Val Val Gly Arg Tyr Ser Val His Asn Ala Gly Ile Ser Phe
            180                 185                 190 tca gtt aaa aaa caa gga gag aca gta gct gat gtt agg aca cta ccc      684
Ser Val Lys Lys Gln Gly Glu Thr Val Ala Asp Val Arg Thr Leu Pro
        195                 200                 205 aat gcc tca acc gtg gac aat att cgc tcc atc ttt gga aat gct gtt      732
Asn Ala Ser Thr Val Asp Asn Ile Arg Ser Ile Phe Gly Asn Ala Val
    210                 215                 220 agt cga gaa ctg ata gaa att gga tgt gag gat aaa acc cta gcc ttc      780
Ser Arg Glu Leu Ile Glu Ile Gly Cys Glu Asp Lys Thr Leu Ala Phe
225                 230                 235                 240
```

```
                                                    -continued
aaa atg aat ggt tac ata tcc aat gca aac tac tca gtg aag aag tgc         828
Lys Met Asn Gly Tyr Ile Ser Asn Ala Asn Tyr Ser Val Lys Lys Cys
                245                 250                 255 atc ttc tta ctc ttc atc aac cat cgt ctg gta gaa tca act tcc ttg         876
Ile Phe Leu Leu Phe Ile Asn His Arg Leu Val Glu Ser Thr Ser Leu
            260                 265                 270 aga aaa gcc ata gaa aca gtg tat gca gcc tat ttg ccc aaa aac aca         924
Arg Lys Ala Ile Glu Thr Val Tyr Ala Ala Tyr Leu Pro Lys Asn Thr
        275                 280                 285 cac cca ttc ctg tac ctc agt tta gaa atc agt ccc cag aat gtg gat         972
His Pro Phe Leu Tyr Leu Ser Leu Glu Ile Ser Pro Gln Asn Val Asp
    290                 295                 300 gtt aat gtg cac ccc aca aag cat gaa gtt cac ttc ctg cac gag gag        1020
Val Asn Val His Pro Thr Lys His Glu Val His Phe Leu His Glu Glu
305                 310                 315                 320 agc atc ctg gag cgg gtg cag cag cac atc gag agc aag ctc ctg ggc        1068
Ser Ile Leu Glu Arg Val Gln Gln His Ile Glu Ser Lys Leu Leu Gly
                325                 330                 335 tcc aat tcc tcc agg atg tac ttc acc cag act ttg cta cca gga ctt        1116
Ser Asn Ser Ser Arg Met Tyr Phe Thr Gln Thr Leu Leu Pro Gly Leu
            340                 345                 350 gct ggc ccc tct ggg gag atg gtt aaa tcc aca aca agt ctg acc tcg        1164
Ala Gly Pro Ser Gly Glu Met Val Lys Ser Thr Thr Ser Leu Thr Ser
        355                 360                 365 tct tct act tct gga agt agt gat aag gtc tat gcc cac cag atg gtt        1212
Ser Ser Thr Ser Gly Ser Ser Asp Lys Val Tyr Ala His Gln Met Val
    370                 375                 380 cgt aca gat tcc cgg gaa cag aag ctt gat gca ttt ctg cag cct ctg        1260
Arg Thr Asp Ser Arg Glu Gln Lys Leu Asp Ala Phe Leu Gln Pro Leu
385                 390                 395                 400 agc aaa ccc ctg tcc agt cag ccc cag gcc att gtc aca gag gat aag        1308
Ser Lys Pro Leu Ser Ser Gln Pro Gln Ala Ile Val Thr Glu Asp Lys
                405                 410                 415 aca gat att tct agt ggc agg gct agg cag caa gat gag gag atg ctt        1356
Thr Asp Ile Ser Ser Gly Arg Ala Arg Gln Gln Asp Glu Glu Met Leu
            420                 425                 430 gaa ctc cca gcc cct gct gaa gtg gct gcc aaa aat cag agc ttg gag        1404
Glu Leu Pro Ala Pro Ala Glu Val Ala Ala Lys Asn Gln Ser Leu Glu
        435                 440                 445 ggg gat aca aca aag ggg act tca gaa atg tca gag aag aga gga cct        1452
Gly Asp Thr Thr Lys Gly Thr Ser Glu Met Ser Glu Lys Arg Gly Pro
    450                 455                 460 act tcc agc aac ccc aga aag aga cat cgg gaa gat tct gat gtg gaa        1500
Thr Ser Ser Asn Pro Arg Lys Arg His Arg Glu Asp Ser Asp Val Glu
465                 470                 475                 480 atg gtg gaa gat gat tcc cga aag gaa atg act gca gct tgt acc ccc        1548
Met Val Glu Asp Asp Ser Arg Lys Glu Met Thr Ala Ala Cys Thr Pro
                485                 490                 495 cgg aga agg atc att aac ctc act agt gtt ttg agt ctc cag gaa gaa        1596
Arg Arg Arg Ile Ile Asn Leu Thr Ser Val Leu Ser Leu Gln Glu Glu
            500                 505                 510 att aat gag cag gga cat gag gtt ctc cgg gag atg ttg cat aac cac        1644
Ile Asn Glu Gln Gly His Glu Val Leu Arg Glu Met Leu His Asn His
        515                 520                 525 tcc ttc gtg ggc tgt gtg aat cct cag tgg gcc ttg gca cag cat caa        1692
Ser Phe Val Gly Cys Val Asn Pro Gln Trp Ala Leu Ala Gln His Gln
    530                 535                 540 acc aag tta tac ctt ctc aac acc acc aag ctt agt gaa gaa ctg ttc        1740
Thr Lys Leu Tyr Leu Leu Asn Thr Thr Lys Leu Ser Glu Glu Leu Phe
545                 550                 555                 560
```

-continued

```
tac cag ata ctc att tat gat ttt gcc aat ttt ggt gtt ctc agg tta    1788
Tyr Gln Ile Leu Ile Tyr Asp Phe Ala Asn Phe Gly Val Leu Arg Leu
            565                 570                 575 tcg gag cca gca ccg ctc ttt gac ctt gcc atg ctt gcc tta gat agt    1836
Ser Glu Pro Ala Pro Leu Phe Asp Leu Ala Met Leu Ala Leu Asp Ser
        580                 585                 590 cca gag agt ggc tgg aca gag gaa gat ggt ccc aaa gaa gga ctt gct    1884
Pro Glu Ser Gly Trp Thr Glu Glu Asp Gly Pro Lys Glu Gly Leu Ala
    595                 600                 605 gaa tac att gtt gag ttt ctg aag aag aag gct gag atg ctt gca gac    1932
Glu Tyr Ile Val Glu Phe Leu Lys Lys Lys Ala Glu Met Leu Ala Asp
610                 615                 620 tat ttc tct ttg gaa att gat gag gaa ggg aac ctg att gga tta ccc    1980
Tyr Phe Ser Leu Glu Ile Asp Glu Glu Gly Asn Leu Ile Gly Leu Pro
625                 630                 635                 640 ctt ctg att gac aac tat gtg ccc cct ttg gag gga ctg cct atc ttc    2028
Leu Leu Ile Asp Asn Tyr Val Pro Pro Leu Glu Gly Leu Pro Ile Phe
            645                 650                 655 att ctt cga cta gcc act gag gtg aat tgg gac gaa gaa aag gaa tgt    2076
Ile Leu Arg Leu Ala Thr Glu Val Asn Trp Asp Glu Glu Lys Glu Cys
        660                 665                 670 ttt gaa agc ctc agt aaa gaa tgc gct atg ttc tat tcc atc cgg aag    2124
Phe Glu Ser Leu Ser Lys Glu Cys Ala Met Phe Tyr Ser Ile Arg Lys
    675                 680                 685 cag tac ata tct gag gag tcg acc ctc tca ggc cag cag agt gaa gtg    2172
Gln Tyr Ile Ser Glu Glu Ser Thr Leu Ser Gly Gln Gln Ser Glu Val
690                 695                 700 cct ggc tcc att cca aac tcc tgg aag tgg act gtg gaa cac att gtc    2220
Pro Gly Ser Ile Pro Asn Ser Trp Lys Trp Thr Val Glu His Ile Val
705                 710                 715                 720 tat aaa gcc ttg cgc tca cac att ctg cct cct aaa cat ttc aca gaa    2268
Tyr Lys Ala Leu Arg Ser His Ile Leu Pro Pro Lys His Phe Thr Glu
            725                 730                 735 gat gga aat atc ctg cag ctt gct aac ctg cct gat cta tac aaa gtc    2316
Asp Gly Asn Ile Leu Gln Leu Ala Asn Leu Pro Asp Leu Tyr Lys Val
        740                 745                 750 ttt gag agg tgt taa atatggttat ttatgcactg tgggatgtgt tcttctttct    2371
Phe Glu Arg Cys
    755 ctgtattccg atacaaagtg ttgtatcaaa gtgtgatata caaagtgtac caacataagt    2431 gttggtagca cttaagactt atacttgcct tctgatagta ttcctttata cacagtggat    2491 tgattataaa taaatagatg tgtcttaaca taa                                 2524

<210> SEQ ID NO 14
<211> LENGTH: 756
<212> TYPE: PRT
<213> ORGANISM: Homo sapiens

<400> SEQUENCE: 14

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60
```

-continued

```
Gly Thr Gly Ile Arg Lys Glu Asp Leu Asp Ile Val Cys Glu Arg Phe
 65                  70                  75                  80

Thr Thr Ser Lys Leu Gln Ser Phe Glu Asp Leu Ala Ser Ile Ser Thr
                 85                  90                  95

Tyr Gly Phe Arg Gly Glu Ala Leu Ala Ser Ile Ser His Val Ala His
                100                 105                 110

Val Thr Ile Thr Thr Lys Thr Ala Asp Gly Lys Cys Ala Tyr Arg Ala
            115                 120                 125

Ser Tyr Ser Asp Gly Lys Leu Lys Ala Pro Lys Pro Cys Ala Gly
130                 135                 140

Asn Gln Gly Thr Gln Ile Thr Val Glu Asp Leu Phe Tyr Asn Ile Ala
145                 150                 155                 160

Thr Arg Arg Lys Ala Leu Lys Asn Pro Ser Glu Glu Tyr Gly Lys Ile
                165                 170                 175

Leu Glu Val Val Gly Arg Tyr Ser Val His Asn Ala Gly Ile Ser Phe
                180                 185                 190

Ser Val Lys Lys Gln Gly Glu Thr Val Ala Asp Val Arg Thr Leu Pro
            195                 200                 205

Asn Ala Ser Thr Val Asp Asn Ile Arg Ser Ile Phe Gly Asn Ala Val
210                 215                 220

Ser Arg Glu Leu Ile Glu Ile Gly Cys Glu Asp Lys Thr Leu Ala Phe
225                 230                 235                 240

Lys Met Asn Gly Tyr Ile Ser Asn Ala Asn Tyr Ser Val Lys Lys Cys
                245                 250                 255

Ile Phe Leu Leu Phe Ile Asn His Arg Leu Val Glu Ser Thr Ser Leu
                260                 265                 270

Arg Lys Ala Ile Glu Thr Val Tyr Ala Ala Tyr Leu Pro Lys Asn Thr
            275                 280                 285

His Pro Phe Leu Tyr Leu Ser Leu Glu Ile Ser Pro Gln Asn Val Asp
            290                 295                 300

Val Asn Val His Pro Thr Lys His Glu Val His Phe Leu His Glu Glu
305                 310                 315                 320

Ser Ile Leu Glu Arg Val Gln Gln His Ile Glu Ser Lys Leu Leu Gly
                325                 330                 335

Ser Asn Ser Ser Arg Met Tyr Phe Thr Gln Thr Leu Leu Pro Gly Leu
                340                 345                 350

Ala Gly Pro Ser Gly Glu Met Val Lys Ser Thr Thr Ser Leu Thr Ser
            355                 360                 365

Ser Ser Thr Ser Gly Ser Ser Asp Lys Val Tyr Ala His Gln Met Val
370                 375                 380

Arg Thr Asp Ser Arg Glu Gln Lys Leu Asp Ala Phe Leu Gln Pro Leu
385                 390                 395                 400

Ser Lys Pro Leu Ser Ser Gln Pro Gln Ala Ile Val Thr Glu Asp Lys
                405                 410                 415

Thr Asp Ile Ser Ser Gly Arg Ala Arg Gln Gln Asp Glu Glu Met Leu
            420                 425                 430

Glu Leu Pro Ala Pro Ala Glu Val Ala Ala Lys Asn Gln Ser Leu Glu
            435                 440                 445

Gly Asp Thr Thr Lys Gly Thr Ser Glu Met Ser Glu Lys Arg Gly Pro
450                 455                 460

Thr Ser Ser Asn Pro Arg Lys Arg His Arg Glu Asp Ser Asp Val Glu
465                 470                 475                 480

Met Val Glu Asp Asp Ser Arg Lys Glu Met Thr Ala Ala Cys Thr Pro
```

-continued

```
                         485                 490                  495
Arg Arg Arg Ile Ile Asn Leu Thr Ser Val Leu Ser Leu Gln Glu Glu
            500                 505                 510

Ile Asn Glu Gln Gly His Glu Val Leu Arg Glu Met Leu His Asn His
            515                 520                 525

Ser Phe Val Gly Cys Val Asn Pro Gln Trp Ala Leu Ala Gln His Gln
    530                     535                 540

Thr Lys Leu Tyr Leu Leu Asn Thr Thr Lys Leu Ser Glu Glu Leu Phe
545                 550                 555                 560

Tyr Gln Ile Leu Ile Tyr Asp Phe Ala Asn Phe Gly Val Leu Arg Leu
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
            595                 600                 605

Glu Tyr Ile Val Glu Phe Leu Lys Lys Lys Ala Glu Met Leu Ala Asp
            610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
                660                 665                 670

Phe Glu Ser Leu Ser Lys Glu Cys Ala Met Phe Tyr Ser Ile Arg Lys
            675                 680                 685

Gln Tyr Ile Ser Glu Glu Ser Thr Leu Ser Gly Gln Gln Ser Glu Val
            690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
                740                 745                 750

Phe Glu Arg Cys
            755
```

METHOD AND KIT FOR DETECTION OF MICROSATELLITE INSTABILITY-POSITIVE CELL

CLAIM OF PRIORITY

The present application claims priority from Japanese application JP 2006-226665 filed on Aug. 23, 2006, the content of which is hereby incorporated by reference into this application.

BACKGROUND OF THE INVENTION

1. Field of the Invention

The present invention relates to a method for detecting a cell having microsatellite instability based on gene expression analysis, which is useful for cancer diagnosis.

2. Background Art

One of the unexpected findings clarified by the human genome project is a report that the number of genes contained in the human genome is much smaller than that has been predicted, and that it is only approximately 25,000. This gene number does not significantly differ from those of lower organisms, and it is insufficient for explanation of the complicated brain system of human and functions of the immune system thereof. Thus, it is considered that various expression mechanisms derived from a single gene play an important role in the complicated biological functions of higher animals.

The variability of the expression of mRNA and a protein from a single gene is mainly controlled by an alternative splicing or a usage of an alternative promoter at the stage of mRNA transcription or RNA processing (see, Non-Patent Document 1). The term "alternative splicing" is used to mean a mechanism for generating several types of mature mRNAs (splicing variants) from a single mRNA precursor as a result of a phenomenon whereby a splicing reaction that generally occurs between splice sites adjacent to each other occurs between various splice sites, when several introns exist in an mRNA precursor. On the other hand, the term "alternative promoter" is used to refer to the presence of several alternative promoters for controlling the transcription of a single gene. When such an alternative promoter exists, several transcription initiation sites are present in the gene. As a result, several types of transcripts having different 5'-terminal sequences are generated. Recently, as a result of searching for 1,780,295 types of full-length cDNA sequences that are contained in an oligo-cap cDNA clones, it has been unexpectedly reported that approximately 52% of genes assigned to the RefSeq database at NCBI, U.S.A. are under the control of alternative promoters, and that 3.1 alternative promoters exist for a single gene on average (see, Non-Patent Document 2). As a result of such a variety of expressions from a single gene, the diversity of organisms or complicated biological functions have been generated in the evolutionary process. On the other hand, it has also been known that such a variety of expressions may cause generation of abnormal proteins or deletion of such a protein itself in individuals, and as a result, it may induce malignant transformation of cells (see, Non-Patent Document 3).

The genetic understanding of hereditary non-polyposis colorectal cancer (HNPCC) has dramatically progressed as a result of discovery of various types of genes associated with mismatch repair. Such a mismatch repair mechanism is a mechanism for recognizing an abnormal base pairing (mismatch base pairs) generated during DNA replication or genetic recombination, and eliminating and repairing the mismatched base pairs. With regard to HNPCC, one of the most typical diseases among familial neoplastic diseases, it has been known that the microsatellite instability (MSI) in the DNA of tumor tissues, which reflects deficiency in a mismatch repair system, is positive in 90% or more of the cases thereof (see, Non-Patent Document 4). The term "microsatellite" is used to mean a repetitive sequence formed by repeating several to several tens of repeat units each consisting of 2 to 5 bases. The term "instability" is used herein to mean a phenomenon in which repeat numbers of microsatellites are abnormally increased or decreased. MSI can be typically detected by assaying microsatellite markers (BAT25, BAT26, D2S123, D5S346, D17S250, etc.) using PCR method. Thus, detection of MSI contributes to HNPCC diagnosis (see, Non-Patent Document 5). In addition, in an international consensus conference regarding MSI detection in 1997, tumor in which instability is detected from two or more markers as mentioned above was defined as MSI-H (a state where 30% or more MSI is detected in tumor), and it was determined that such tumor has clinicopathologic characteristics.

Genetic diagnosis of cancer is based on the results of analysis of mutation of a causative gene in many cases. However, differing from familial adenomatous polyposis (FAP) whose single causative gene is APC, five causative genes have been identified (hMSH2, hMLH1, hPMS1, hPMS2, and hMSH6) in the case of HNPCC. However, since the ratio of developing the disease (penetrance rate) when such causative genes are mutated is not 100%, the genetic diagnosis of HNPCC based on mutation of the aforementioned causative genes has not yet reached a clinical level at the present time, and it is considered that such genetic diagnosis is still at a study level in the classification of American Society of Clinical Oncology (ASCO). With regard to cancer-associated genes such as hMLH1, a method, which comprises detecting genetic mutation or methylation on their genomic sequences and detecting cancer using such genetic mutation or methylation as an indicator, has been proposed (Patent Documents 1 and 2). However, the disease cover ratio of this method is not very high, and the method has also been problematic in terms of simplicity and promptness. Hence, it has been desired that a simple and highly reliable method for testing cells, which is useful for the diagnosis of cancers such as HNPCC as a typical example, be developed. If a cell test method capable of screening of cancer at a gene expression level were developed, it means that the real-time detection system in that method would be effective. However, such a useful test method has not yet been developed.

[Patent Document 1] JP Patent Publication (Kokai) No. 2005-304497 A

[Patent Document 2] JP Patent Publication (Kohyo) No. 2002-533061 A

[Non-Patent Document 1] Landry J. R. et al., Trends in Genetics, (2003) 19(11) p. 640-648

[Non-Patent Document 2] Kimura K. et al., Genome Research, (2006) 16: p. 55-65

[Non-Patent Document 3] Brinkman B. M., Clin. Biochem., (2004) 37(7): p. 584-594

[Non-Patent Document 4] Liu B. et al., Nature Med., (1996) 2: p. 169-174

[Non-Patent Document 5] Laiho P. et al., Cancer Research, (2002) 62: p. 1166-1170

[Non-Patent Document 6] Deng G. et al., Cancer Research, (1999) 59: p. 2029-2033

SUMMARY OF THE INVENTION

It is an object of the present invention to provide a method for testing a cell based on gene expression analysis, which is useful for cancer diagnosis.

As a result of concentrated studies for achieving the aforementioned object, the present inventors have found that at least 3 types of transcriptional variants (variant type 1, variant type 2, and variant type 3) are expressed from a human MLH1 gene (hMLH1 gene), and further that in a cancer cell positive for microsatellite instability, the expression level of variant type 3 is relatively higher than that of variant type 1 that is a major transcript, thereby completing the present invention.

That is to say, the present invention includes the following embodiments.

[1] A gene expression analysis method comprising: measuring the expression level of a transcript of a human MLH1 gene containing the nucleotide sequence as shown in SEQ ID NO: 1 at the 5' terminus thereof and the expression level of a transcript of a human MLH1 gene containing the nucleotide sequence as shown in SEQ ID NO: 2 at the 5' terminus, in a biological sample; and comparing the expression levels, thereby detecting a cell positive for microsatellite instability.

In this method, the expression level of the transcripts can be measured using a real-time PCR method. The measurement using the real-time PCR method can be preferably carried out by TaqMan® probe method.

In the method of the present invention, the measurement is also preferably carried out using the following primer pairs (a) and (b):

(a) a primer pair, which is a combination of a primer comprising a nucleotide sequence consisting of 15 to 50 contiguous nucleotides comprising a portion of an exon 1 sequence spanning from nucleotides 1 to 183 from the nucleotide sequence as shown in SEQ ID NO: 1, with a primer comprising a nucleotide sequence complementary to a nucleotide sequence consisting of 15 to 50 contiguous nucleotides from an exon 2 sequence as shown in SEQ ID NO: 5; and (b) a primer pair, which is a combination of a primer comprising a nucleotide sequence consisting of 15 to 50 contiguous nucleotides comprising a portion of exon 1 and 2 spanning from nucleotides 1 to 132 from the nucleotide sequence as shown in SEQ ID NO: 2, with a primer comprising a nucleotide sequence complementary to a nucleotide sequence consisting of 15 to 50 contiguous nucleotides from a exon 2 sequence as shown in SEQ ID NO: 5.

Preferred examples of the above primer pairs (a) and (b) include:

the primer pair (a), which is a combination of a primer comprising the nucleotide sequence as shown in SEQ ID NO: 6 with a primer comprising the nucleotide sequence as shown in SEQ ID NO: 7, and the primer pair (b), which is a combination of a primer comprising the nucleotide sequence as shown in SEQ ID NO: 8 with a primer comprising the nucleotide sequence as shown in SEQ ID NO: 7. In the case of using the TaqMan® probe method in the measurement using such primer pairs, a probe comprising the nucleotide sequence as shown in SEQ ID NO: 9, to one end of which a fluorescent substance is added and to the other end of which a quenching substance is added, can be preferably used.

The cell positive for microsatellite instability, which is detected by the above described method of the present invention, is a cancer cell in many cases. This cancer may be colorectal cancer. Further, this colorectal cancer may be hereditary non-polyposis colorectal cancer.

[2] A primer set for use in analyzing a gene expression level to detect a cell positive for microsatellite instability, comprising the following primer pairs (a) and (b):

(a) a primer pair, which is a combination of a primer comprising a nucleotide sequence consisting of 15 to 50 contiguous nucleotides comprising a portion of an exon 1 sequence spanning from nucleotides 1 to 183 the nucleotide sequence as shown in SEQ ID NO: 1, with a primer comprising a nucleotide sequence complementary to a nucleotide sequence consisting of 15 to 50 contiguous nucleotides from an exon 2 sequence as shown in SEQ ID NO: 5; and (b) a primer pair, which is a combination of a primer comprising a nucleotide sequence consisting of 15 to 50 contiguous nucleotides comprising a portion of exon 1 and 2 spanning from nucleotides 1 to 132 from the nucleotide sequence as shown in SEQ ID NO: 2, with a primer comprising a nucleotide sequence complementary to a nucleotide sequence consisting of 15 to 50 contiguous nucleotides from an exon 2 sequence as shown in SEQ ID NO: 5.

[3] A kit for analyzing a gene expression level to detect a cell positive for microsatellite instability, comprising the following primer pairs (a) and (b):

(a) a primer pair, which is a combination of a primer comprising a nucleotide sequence consisting of 15 to 50 contiguous nucleotides comprising a portion of an exon 1 sequence spanning from positions 1 to 183 from the nucleotide sequence as shown in SEQ ID NO: 1, with a primer comprising a nucleotide sequence complementary to a nucleotide sequence consisting of 15 to 50 contiguous nucleotides from an exon 2 sequence as shown in SEQ ID NO: 5; and (b) a primer pair, which is a combination of a primer comprising a nucleotide sequence consisting of 15 to 50 contiguous nucleotides comprising a portion of exon 1 and 2 spanning from positions 1 to 132 from the nucleotide sequence as shown in SEQ ID NO: 2, with a primer comprising a nucleotide sequence complementary to a nucleotide sequence consisting of 15 to 50 contiguous nucleotides from an exon 2 sequence as shown in SEQ ID NO: 5.

The primer pairs (a) and (b) contained in this kit are preferably:

the primer pair (a), which is a combination of a primer comprising the nucleotide sequence as shown in SEQ ID NO: 6 with a primer comprising the nucleotide sequence as shown in SEQ ID NO: 7, and the primer pair (b), which is a combination of a primer comprising the nucleotide sequence as shown in SEQ ID NO: 8 with a primer comprising the nucleotide sequence as shown in SEQ ID NO: 7.

This kit may further comprise a probe comprising the nucleotide sequence as shown in SEQ ID NO: 9, to one end of which a fluorescent substance is added and to the other end of which a quenching substance is added.

The above described cell that is a detection target of this kit is preferably a cancer cell. This kit is particularly useful as a kit for diagnosing cancer, is more particularly useful as a kit for diagnosing colorectal cancer, and further more particularly useful as a kit for diagnosing hereditary non-polyposis colorectal cancer.

The detection method of the present invention is capable of simply and clearly testing the expression level of an hMLH1 gene even in a case where the above method is applied to a biological sample that contains only small quantities of cancer cells. Thus, the above method is capable of rapidly and simply detecting a cell positive for microsatellite instability, in particular, a cancer cell.

BRIEF DESCRIPTION OF THE DRAWINGS

In FIG. 2B, when the expression level of variant type 1 was lower than that of variant type 3, it was indicated as V1<V3, when variant type 1 was not detected and only variant type 3 was detected, it was indicated as V1(−), V3(+), and when the expression level of variant type 1 was higher than that of variant type 3, it was indicated as V1>V3. In addition, in FIG. 2B, whether microsatellite instability (MSI) is positive (+) or negative (−), and whether methylation was observed (+) or was not observed (−) in the promoter region of the hMLH1 gene, are also shown.

DETAILED DESCRIPTION OF THE INVENTION

The present invention will be described in detail below.

A human MLH1 gene (hMLH1 gene) is a human homolog (homologue) of the DNA mismatch repair gene, mutL, of *Escherichia coli* (*E. coli*). The hMLH1 gene has been known as a gene locus in which mutation occurs with high frequency in hereditary non-polyposis colorectal cancer (HNPCC). The RefSeq sequence of the MRNA of the hMLH1 gene is submitted to GenBank under Accession No. NM000249. In the present specification, the RefSeq sequence is shown in SEQ ID NO: 13 for reference. This RefSeq sequence (SEQ ID NO: 13) of the mRNA of the hMLH1 gene contains 19 exons.

Figure 1:
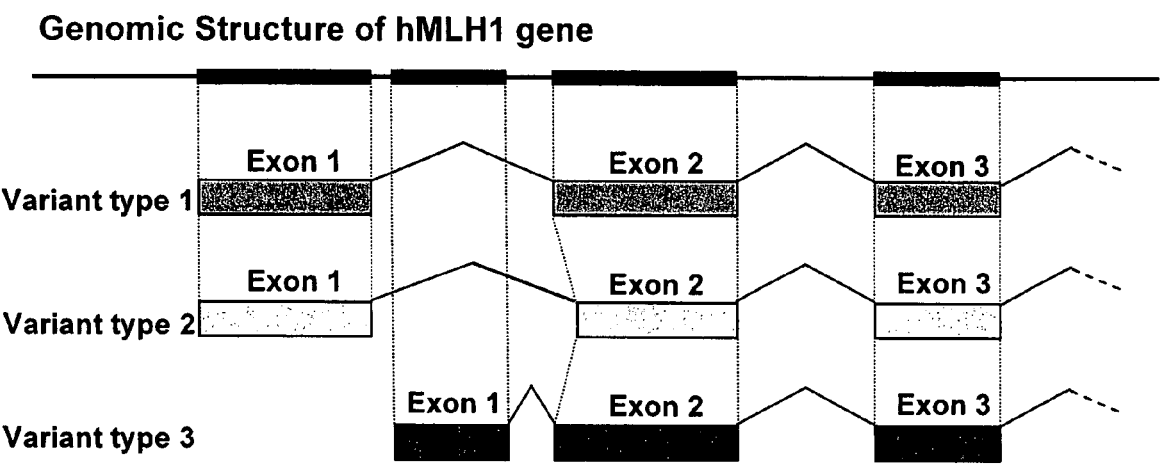
FIG. 1 sets forth the exon structures of 3 types of transcripts of the hMLH1 gene.

In the present invention, as a variant of the transcript of the hMLH1 gene, variant type 2 and variant type 3 were discovered, in addition to variant type 1 which is a major transcript and almost corresponds to the aforementioned RefSeq sequence (FIG. 1). This variant type 1 contains the nucleotide sequence as shown in SEQ ID NO: 1 (exon 1 and 2) at the 5' terminus thereof, followed by the sequence of exon 3 to 19 of the hMLH1 gene, which corresponds to nucleotides 268 to 2524 of SEQ ID NO: 13. Variant type 2 has an exon structure that is almost the same as that of variant type 1, but 5 nucleotides at the 5' end of the exon 2 (SEQ ID NO: 5) have been deleted. On the other hand, variant type 3 is derived from an mRNA precursor transcribed from a transcription initiation site that is located at approximately 300 bp downstream from that of variant type 1, and thus the 5' terminus of variant type 3 comprises the nucleotide sequence of SEQ ID NO: 2 (exon 1 and 2) that differs from that of variant type 1, and exon 3 to 19 sequences that are shared with variant types 1 and 2 follow backward. Since there exist a translation initiation site, ATG in the sequence of exon 1 of variant type 1, an amino acid sequence at N-terminus encoded by variant type 3 differs from that by variant type 1. It is predicted that such a protein encoded by variant type 3 will be produced as a defective protein, or such a protein will not be produced at all.

In the present invention, it was also shown that the expression level of variant type 3 was relatively increased when compared with the expression level of the aforementioned variant type 1, in cancer cells such as colorectal cancer, and particularly, in cells positive for microsatellite instability. It is considered that the expression of variant type 1 is generally found in the largest amount in vivo. Thus, a change in the ratio between the expression levels of the transcript of the hMLH1 gene shows abnormality in the expression state of the hMLH1 gene in cells in a biological sample. Such abnormality was considered to be correlated with microsatellite instability and malignant transformation in cells.

The method of the present invention is based on the aforementioned findings. The present method is a gene expression analysis method, comprising: measuring the expression level of variant type 1 (a transcript of the human MLH1 gene containing the nucleotide sequence as shown in SEQ ID NO: 1 at the 5' terminus) and the expression level of variant type 3 (a transcript of the human MLH1 gene containing the nucleotide sequence as shown in SEQ ID NO: 2 at the 5' terminus), in a biological sample; and making a comparison between the expression levels, thereby detecting cells which are positive for microsatellite instability.

In the present invention, a biological sample may be any tissue, cell, or body fluid, collected from a human subject. Examples of the biological sample may include skin, mucosal tissues, and gastrointestinal tissues. Such examples may also include blood, lymph, saliva, and seminal fluid. Preferred biological samples may particularly include tumor, cancer tissues, and tissues that are suspected of becoming malignant transformed. The biological sample may be an established cultured cell line. Particularly preferred biological samples may include tissues or cells derived from colorectal cancer, and colorectal tissues or cells that are suspected to be affected by colorectal cancer, which may be, but not limited to, for example, hereditary non-polyposis colorectal cancer (HNPCC).

The term "transcript" is used herein include an mRNA precursor transcribed from a certain gene, a modified product of such an mRNA precursor (which is modified by addition of a cap structure, polyadenylation, etc.), mature mRNA, and cDNA reversely transcribed from mature RNA. When RNA is referred to as a transcript, "T" (thymine) in the nucleotide sequence as shown in each sequence number used to specify the transcript is read as "U" (uracil). The term "the expression level of a transcript (variant)" is used herein to mean the abundance of a transcript that is expressed from a certain gene in a biological sample.

The expression levels of the transcript, variant type 1 and variant type 3, contained in a biological sample, may be measured according to a known method in the art of the present invention. Examples of the method of measuring an expression level may include, but not limited to, the real-time PCR method, the semi-quantitative RT-PCR method, the competitive PCR method using a capillary electrophoresis apparatus, a gene expression level measurement method using a DNA chip or microarray, differential display method, and the Northern blot method. Using such methods, the abundance of each transcript contained in a nucleic acid sample (e.g. RNA or cDNA) prepared from a biological sample can be measured. Such a nucleic acid sample may be prepared from a biological sample according to a routine method, and it may also be purified before analysis. In the present invention, genomic DNA or RNA may be prepared in accordance with standard experimental instructions used in the molecular biological field, such as J. Sambrook et al. (Eds.), Molecular Cloning, 3rd ed. Cold Spring Harbor Laboratory Press (2001).

Any type of method can be used to measure the expression levels of variant type 1 and variant type 3, as long as it is able to conduct an assay while distinguishing a transcript from another transcript. In the present invention, determination quantity of the exon 1 whose sequence is significantly different between variant type 1 and variant type 3 is conveniently used, for example.

As an example, the measurement of an expression level using the real-time PCR method will be described in detail. The real-time PCR method is a technique of monitoring an increase in a PCR amplified product in real time and then analyzing it. In general, the above method is carried out using a real-time PCR apparatus formed by unifying a thermal cycler and a spectrophotofluorometer. When compared with the conventional PCR method, the real-time PCR does not need electrophoresis. Thus, the real-time PCR enables rapid and easy analysis, and further it is excellently quantitative. The principle of an assay by the real-time PCR method is as follows. First, known amounts of DNA that have been subjected to serial dilution are used as standard samples. While performing PCR, the amounts of a PCR product in each of the standard samples are monitored, and the number of cycles (threshold cycle; Ct value), at which each dilution sample becomes a certain amount of amplified product in an exponential amplification phase, is detected. The number of cycles is plotted on a horizontal axis, and the amount of an initial template in the standard sample is then plotted on a vertical axis, so as to produce a calibration curve. Further, regarding a test nucleic acid sample containing an unknown concentration of a transcript, the amount of a PCR product is monitored with performing a PCR reaction under the same conditions as those for the standard sample, the number of cycles (Ct value) of the same amplification product amount as above is obtained. The Ct value obtained in the test nucleic acid sample is applied to the calibration curve as obtained above, and thus the amount of an initial template contained in the test nucleic acid sample can be estimated. This initial template amount corresponds to the expression level of a transcript.

Monitoring (detection) of a PCR product in the real-time PCR is preferably carried out using a fluorescent substance, but a monitoring method is not limited thereto. As such a fluorescence monitoring method, known techniques such as the intercalator method or the TaqMan® probe method can be used, but examples of such a method are not limited thereto. The intercalator method comprises addition of SYBR® Green I that is a substance emitting fluorescence as a result of binding to double-stranded DNA (intercalator), to a real-time PCR reaction system. In this method, an intercalator binds to double-stranded DNA synthesized by a PCR reaction and it emits florescence as a result of irradiation with excitation light. Thus, the intensity of such fluorescence is measured, so as to monitor the amount of a PCR amplified product generated. Since any given double-stranded DNA is detected by this intercalator method, the method does not require production of a detection probe for each gene. Thus, the experiment cost is inexpensive, and a reaction system is easily constructed. However, the detection specificity is not very high. On the other hand, the TaqMan® probe method is a method, which comprises addition of an oligonucleotide probe (TaqMan® probe), which is typically labeled with (bound to) a fluorescent substance (FAM, etc.) at the 5'-terminus and a quenching substance (TAMRA etc.) at the 3'-terminus, to a real-time PCR reaction system. In this method, the TaqMan® hybridizes specifically with template DNA in an annealing step. At that time, since a fluorescent substance and a quenching substance coexist on the probe, development of fluorescence is suppressed, although excitation light is emitted from the fluorescent substance. However, when the TaqMan® probes hybridizing with the templates are successively removed by the 5'→3' exonuclease activity of Taq DNA polymerase in the subsequent elongation step, the fluorescent substances are released from the probes, and suppression by the quenching substances is removed, so as to generate fluorescence. By measuring such fluorescence intensity, the amount of amplified PCR product can be monitored. This TaqMan® probe method causes a high experiment cost, but it has high detection specificity and is excellently (or particularly) quantitative.

In the method of the present invention, a quantitative assay that is based on the aforementioned real-time PCR method can preferably be used to measure the expression level of each variant. In such a case, the TaqMan® probe method can preferably be used to monitor the PCR amplification product, but the usable method is not limited thereto. In the TaqMan® probe method, a TaqMan® probe, to one end (generally 5'-terminus) of which a fluorescent substance is added and to the other end (generally 3'-terminus) of which a quenching substance is added, is used. This probe is designed such that it can be annealed to a PCR amplification product that is generated by real-time PCR. As a fluorescent substance added to the probe, FAM or VIC can be used. As a quenching substance, TAMRA or the like can be used. Reaction conditions applied in the real-time PCR can be determined by persons skilled in the art, as appropriate. The reaction conditions as described later in the examples can also be used.

In the method of the present invention, in order to measure the expression level of each variant, the following primer pair (a) is used for specifically amplifying variant type 1 in PCR and the following primer pair (b) is used for specifically amplifying variant type 3 in PCR, so as to amplify both variants:

(a) a primer pair, which is a combination of a primer comprising a nucleotide sequence consisting of 15 to 50 contiguous nucleotides comprising a portion (preferably 10 or more base pairs in length, for example, 10 to 30 base pairs in length) of an exon 1 sequence spanning from nucleotides 1 to 183 (This region is better for designing PCR primers than any other region. This region corresponds to the region of the almost all the sequence of exon 1 shown in SEQ ID NO: 1 and includes 3' end of appropriate sense primer for amplifying variant type 1 shown in SEQ ID NO: 6) from the nucleotide sequence as shown in SEQ ID NO: 1, with a primer comprising a nucleotide sequence complementary to a nucleotide sequence consisting of 15 to 50 contiguous nucleotides from an exon 2 sequence as shown in SEQ ID NO: 5; and (b) a primer pair, which is a combination of a primer comprising a nucleotide sequence consisting of 15 to 50 contiguous nucleotides comprising a portion (for example, 10 to 30 base pairs in length) of exon 1 and 2 spanning from nucleotides 1 to 132 (This region is better for designing PCR primers than any other region. This region corresponds to the region containing the whole sequence of exon 1 and 5'end of exon 2 shown in SEQ ID NO:2 and includes 3' end of appropriate sense primer for amplifying variant type 3 shown in SEQ ID NO:8) from the nucleotide sequence as shown in SEQ ID NO: 2, with a primer comprising a nucleotide sequence complementary to a nucleotide sequence consisting of 15 to 50 contiguous nucleotides from an exon 2 sequence as shown in SEQ ID NO: 5.

With regard to such primer pairs (a) and (b), a specific example is preferably as follows:

primer pair (a): a combination of a primer having the nucleotide sequence as shown in SEQ ID NO: 6 with a primer having the nucleotide sequence as shown in SEQ ID NO: 7, and primer pair (b): a combination of a primer having the nucleotide sequence as shown in SEQ ID NO: 8 with a primer having the nucleotide sequence as shown in SEQ ID NO: 7.

When the expression levels of the aforementioned variant types 1 and 3 are measured by real-time PCR that is based on the TaqMan® probe method, using a combination of primers having the sequences as shown in SEQ ID NOS: 6 to 8, a probe having the nucleotide sequence as shown in SEQ ID NO: 9, to one end (generally 5'-terminus) of which a fluorescent substance is added and to the other end (generally 3'-terminus) of which a quenching substance is added, is particularly preferably used as a TaqMan® probe.

A method of measuring the expression level of a variant, using such primers and probes, comprises the following steps, for example:

a step of amplifying variant type 1 from cDNA derived from a biological sample, using a primer having the nucleotide sequence as shown in SEQ ID NO: 6 and a primer having the nucleotide sequence as shown in SEQ ID NO: 7;

a step of amplifying variant type 3 from cDNA derived from a biological sample, using a primer having the nucleotide sequence as shown in SEQ ID NO: 8 and a primer having the nucleotide sequence as shown in SEQ ID NO: 7; and a step of monitoring the amount of the PCR amplification product in each amplification reaction, and then calculating the initial content of variant type 1 and that of variant type 3 in the biological samples.

In this monitoring step, the TaqMan® probe is added to each amplification reaction system, so that the amount of a PCR amplification product can be measured by fluorescence intensity.

In the method of the present invention, after the expression level of variant type 1 and that of variant type 3 have been measured as described above, a comparison is made between both expression levels, so as to detect a cell positive for microsatellite instability. Specifically, when the expression level of variant type 1 is compared with that of variant type 3, if the measurement value of the expression level of variant type 3 is higher than the measurement value of the expression level of variant type 1, there is a high possibility that a cell positive for microsatellite instability may be contained in the biological sample examined. Even when variant type 1 is not detected and only variant type 3 is detected, it is deemed that the expression level of variant type 3 is higher than that of variant type 1. In such a case, it can be determined that a cell positive for microsatellite instability may be contained in the biological sample examined. Thus, in the method of the present invention, the presence of a cell positive for microsatellite instability can be detected in a biological sample collected from a subject.

Microsatellite instability is a phenomenon whereby the repeat number of repeat units (microsatellites) consisting of 2 to 5 nucleotides on the genome increases or decreases abnormally. Severe microsatellite instability occurs in 12% to 16% of all types of colorectal cancers, and in 90% or more of hereditary non-polyposis colorectal cancer. Such microsatellite instability is observed in various types of cancers such as cancer of uterine body, stomach cancer, esophageal cancer, multiple primary cancer, lymphoid tumor, or squamous cell carcinoma. Thus, microsatellite instability has a strong correlation with cancers. Since it is considered that microsatellite instability occurs due to a deficiency in a DNA mismatch repair mechanism, when such microsatellite instability is exhibited, there is a concern regarding a tendency to develop multiple cancers or poor prognosis. Accordingly, when a cell positive for microsatellite instability is detected by the method of the present invention, it can be determined that there is a high possibility that the cell may be a cancer cell. Detected cell like this positive for microsatellite instability may be a cancer cell, in particular, a cell of cancer such as colorectal cancer, hereditary non-polyposis colorectal cancer, cancer of uterine body, stomach cancer, esophageal cancer, multiple primary cancer, lymphoid tumor, squamous cell carcinoma, endometrial cancer, or pancreatic cancer, and preferably, colorectal cancer, and particularly preferably hereditary non-polyposis colorectal cancer. Thus, the present invention also relates to a method of detecting a cancer cell, which comprises measuring the expression level of variant type 1 of the hMLH1 gene and the expression level of variant type 3 thereof in a biological sample, and making a comparison between such expression levels.

In addition, the present invention also relates to a primer set comprising primer pairs (a) and (b), which can preferably be used in the aforementioned method. These primers sets are ones for use in the analysis of a gene expression level for the purpose of the detection of a cell positive for microsatellite instability, which is a combination of the following primer pairs (a) and (b):

(a) a primer pair, which is a combination of a primer comprising a nucleotide sequence consisting of 15 to 50 contiguous nucleotides comprising a portion (for example, 10 to 30 base pairs in length) of an exon 1 sequence spanning from nucleotides 1 to 183 from the nucleotide sequence as shown in SEQ ID NO: 1, with a primer comprising a nucleotide sequence complementary to a nucleotide sequence consisting of 15 to 50 contiguous nucleotides from an exon 2 sequence as shown in SEQ ID NO: 5; and (b) a primer pair, which is a combination of a primer comprising a nucleotide sequence consisting of 15 to 50 contiguous nucleotides comprising a portion (for example, 10 to 30 base pairs in length) of exon 1 and 2 spanning from nucleotides 1 to 132 from the nucleotide sequence as shown in SEQ ID NO: 2, with a primer comprising a nucleotide sequence complementary to a nucleotide sequence consisting of 15 to 50 contiguous nucleotides from an exon 2 sequence as shown in SEQ ID NO: 5.

A specific example of such a primer set is a combination of primers, which includes:
a primer comprising the nucleotide sequence as shown in SEQ ID NO: 6;
a primer comprising the nucleotide sequence as shown in SEQ ID NO: 7; and
a primer comprising the nucleotide sequence as shown in SEQ ID NO: 8.

These primers can be easily produced by an oligonucleotide synthesis technique known in the art, or by the PCR method using, as a template, a sequence contained in the aforementioned hMLH1 gene variant types 1 and 3, such as SEQ ID NO: 1 or 2, or other methods. The "primer" of the present invention may be labeled so as to be favorably used in detection, as long as it can be used in PCR or the like. For example, the primer of the present invention may be a polynucleotide, to the 5'- or 3'-terminus of which a marker such as a fluorescence dye, enzyme, protein, radioactive isotope, chemiluminescence substance, or biotin, has been added. In the present invention, an oligonucleotide that is added to a polynucleotide so as to be used in detection (for example, the sequence "flap" irrelevant to a template, used in the invader method for mutation detection) is also included in such a "marker."

Moreover, the present invention also relates to a kit for analyzing a gene expression level, which is used for detection of a cell positive for microsatellite instability, and which comprises the aforementioned primer pairs (a) and (b). This kit may further comprise a TaqMan®, which is a probe comprising the nucleotide sequence as shown in SEQ ID NO: 9, to one end of which a fluorescent substance is added and to the other end of which a quenching substance is added. The detection target of this kit is preferably a cancer cell, and in particular, this kit can be used in detection of a cancer cell positive for microsatellite instability. Accordingly, this kit is useful as a kit for diagnosing cancer. Further, this kit can be advantageously used as a kit for diagnosing colorectal cancer, and particularly hereditary non-polyposis colorectal cancer (HNPCC).

EXAMPLES

The present invention will be more specifically described in the following examples. However, these examples are not intended to limit the technical scope of the present invention.

Example 1

Searching for Transcriptional Variants of hMLH1 Gene

In order to examine a possibility that the hMLH1 gene would be expressed as several transcriptional variants (mutants) as a result of alternative splicing or the usage of an alternative promoter, the present inventors conducted the following experiment.

As described in Non-Patent Document 2, sequence information of approximately 1,800,000 of human full-length cDNAs including the 5'-terminus has been revealed based on the obtainment of human gene full-length cDNAs by construction of a cDNA clones using the oligo-cap method (Suzuki and Sugano (2003) Methods Mol. Biol. 221: p. 73-91). Such sequence information has been assigned to GenBank, and it is disclosed to the public. The present inventors collected such sequence information from GenBank, and they formatted it into multi-FASTA. Thereafter, homologous searching was performed against the thus obtained sequence data with a blastn program, using the RefSeq sequence (NCBI Reference Sequence) of hMLH1 mRNA (GenBank Accession No. NM_000249; SEQ ID NO: 13) as a query. Among the sequences of a high degree of similarity, sequences having an E-value of $10^{-10}$ or less were selected as hMLH1-associated cDNA sequences. Subsequently, a sequence corresponding to a region that is assigned to the hMLH1 gene in human 3rd chromosome was selected from GenBank human genomic sequence database Build 35. This genomic sequence of the hMLH1 gene and each hMLH1-associated cDNA sequence selected as described above were processed with b12seq of the BLAST program, so as to obtain an alignment for each case. Subsequently, the alignments that were correctly aligned ahead of 2nd exonic region of hMLH1 RefSeq (a sequence corresponding to nucleotides 177 to 267 of NM_000249) and that were also closely matched (the identity is 98% or more) were selected among the whole alignments. The selected alignments were analyzed. As a result, 3 patterns were observed in terms of the correlation between the hMLH1-associated cDNA sequence and the hMLH1 genomic sequence. That is to say, it was revealed that there are at least 3 types of variations (namely, variant types 1, 2, and 3) in terms of the transcripts of the hMLH1 gene. The structure on the 5'-terminal side of each of these 3 types of transcripts are shown in FIG. 1. It is to be noted that only the first 3 exons out of 19 exons are shown in FIG. 1.

As shown in FIG. 1, exon 1, exon 2, and exon 3 are included in this order from the 5'-terminal end in transcriptional variant type 1. A translation initiation site (ATG) is located in exon 1. As a result of this analysis, it was clarified that the nucleotide sequence of NM000249 that is the RefSeq sequence of the hMLH1 gene lacks only a little portion of the 5'-terminus sequence of the exon 1 of variant type 1. In contrast, variant type 2 has almost the same exonic structure as that of variant type 1, but the exon 2 of variant type 2 is 5 nucleotides shorter than that of variant type 1 on the 5'-terminal end. Thus, it was clarified that variant type 2 is an alternative splicing variant. Further, the exon 2 and 3 sequences of variant type 3 are the same as those of variant type 1, but the sequence of exon 1 of variant type 3 is completely different from those of variant type 1 and variant type 2. As a result, it was found that the hMLH1 gene is controlled by an alternative promoter, and thus the transcription of variant type 3 is found to be started approximately 300 bp downstream from a transcription initiation site of variant type 1.

It was shown from the aforementioned analysis that there are found 141 variant type 1 (75%), 14 variant type 2 (7.4%), and 32 variant type 3 (17.1%) in the selected hMLH1-associated cDNA sequences, and that variant type 1 is the most major transcript. The hMLH1-associated cDNA sequences classified into each variant are shown in Table 1. Each hMLH1-associated cDNA sequence is represented by GenBank Accession No. in Table 1.

TABLE 1

| accession number | | | | | | | |
|---|---|---|---|---|---|---|---|
| variant 1 | | | | | variant 2 | variant 3 | |
| AU131219 | DA031179 | DA050403 | DA110166 | DB243737 | DA385243 | AU127122 | DA517219 |
| AU127758 | DA716690 | DA125431 | DB040429 | DA909925 | DA868597 | DA935122 | DA343206 |
| DA619769 | DA472218 | DA043349 | DA880601 | DA453337 | DA815001 | DB253300 | |
| DA024420 | DA983131 | DA695612 | DA475144 | DA055019 | DA070867 | DB204422 | |
| DA953555 | DA702671 | DB272759 | DA762271 | DA209147 | DB139980 | DA930241 | |
| DA023897 | DA701340 | DB090691 | DA503831 | DA914770 | DB287548 | DA566031 | |
| DA486475 | DB200826 | DA556556 | DA494857 | DA472331 | DB157098 | DA814707 | |
| DA932049 | DA304561 | DB274178 | DB252001 | DA609156 | DB012065 | DA166268 | |
| DA426942 | DA658037 | DA659112 | DB120181 | DA752464 | DB114802 | DA748219 | |
| DA555173 | DA624450 | DB270772 | DA666173 | DB014982 | DB018927 | DA927898 | |
| DA479521 | DA489729 | DB269584 | DA631956 | DA958303 | DA866298 | DA921733 | |
| DA524635 | DA476333 | DA559708 | DA518707 | DA952805 | DA352218 | DA963961 | |
| DA447945 | AU280370 | DA913772 | DA698928 | DA783187 | DA506267 | DA430514 | |
| DA952842 | DA374168 | DA619525 | DB246315 | DA884873 | DB252510 | DA303777 | |
| DA350100 | DA201970 | DA478068 | DA106361 | DA794400 | | DA664790 | |
| DA915432 | DA577087 | DA503277 | DA712069 | DA287058 | | DA922309 | |
| DA790495 | DA926525 | DA937827 | DA493353 | DB040297 | | DA476068 | |
| DA050020 | DA814813 | DA650335 | DA911958 | DA348650 | | DA580525 | |
| DA729732 | DB011897 | DA554567 | DA765712 | DA086654 | | DB012054 | |
| DA972163 | DA582565 | DA690019 | DA656699 | DA660079 | | DA296090 | |
| DA563477 | DA287218 | DA738557 | DA592612 | DA510241 | | DB259565 | |
| DA707133 | DA173423 | DA262636 | DB266774 | | | DA955738 | |

TABLE 1-continued

| | | | accession number | | | | |
|---|---|---|---|---|---|---|---|
| | variant 1 | | | | variant 2 | variant 3 | |
| AU128432 | DA501808 | DA819642 | DA877866 | | | DA821467 | |
| DA555707 | DA881017 | DA356018 | DB055056 | | | DA275297 | |
| DB092229 | DB000482 | DA919830 | DA887994 | | | DA172498 | |
| DA555444 | DA546685 | DA751926 | DA997466 | | | DA582466 | |
| DA880449 | DA349545 | DA207023 | DA874359 | | | DA750838 | |
| DA033654 | DB008432 | DA659014 | DA478450 | | | DA749519 | |
| DA305360 | DA970996 | DA599881 | DB089707 | total | total | DA073874 | total |
| DA013759 | DA308229 | DA503294 | DA004869 | 141 clones | 14 clones | DA156778 | 32 clones |

The nucleotide sequences of the exon 1 and 2 portions of variant type 1 and variant type 3, which were discovered in the present examples, are shown in Table 2.

TABLE 2

| | |
|---|---|
| Variant type 1, exon 1 (SEQ ID NO: 3) | AAGAACGTGAGCACGAGGCACT GAGGTGATTGGCTGAAGGCACT TCCGTTGAGCATCTAGACGTTT CCTTGGCTCTTCTGGCGCCAAA ATGTCGTTCGTGGCAGGGGTTA TTCGGCGGCTGGACGAGACAGT GGTGAACCGCATCGCGGCGGGG GAAGTTATCCAGCGGCCAGCTA ATGCTATCAAAGAGATGATTGA GAACTG |
| Variant type 3, exon 1 (SEQ ID NO: 4) | GCATGCCCACAACGGCGGAGGC CGCCGGGTTGCCTGACGTGCCA GTCAGGCCTTCTCCTTTTCCGC AGACCGTGTGTTTCTTTACCGC TCTCCCCCGAGACCTTTTAAGG GTTGTTTGGAGT |
| Variant types 1 and 3, exon 2 (SEQ ID NO: 5) | TTTAGATGCAAAATCCACAAGT ATTCAAGTGATTGTTAAAGAGG GAGGCCTGAAGTTGATTCAGAT CCAAGACAATGGCACCGGGATC AGG |
| Variant type 1, exons 1+ 2 (SEQ ID NO: 1) | AAGAACGTGAGCACGAGGCACT GAGGTGATTGGCTGAAGGCACT TCCGTTGAGCATCTAGACGTTT CCTTGGCTCTTCTGGCGCCAAA ATGTCGTTCGTGGCAGGGGTTA TTCGGCGGCTGGACGAGACAGT GGTGAACCGCATCGCGGCGGGG GAAGTTATCCAGCGGCCAGCTA ATGCTATCAAAGAGATGATTGA GAACTGTTTAGATGCAAAATCC ACAAGTATTCAAGTGATTGTTA AGAGGGAGGCCTGAAGTTGAT TCAGATCCAAGACAATGGCACC GGGATCAGG |
| Variant type 3, exons 1 + 2 (SEQ ID NO: 2) | GCATGCCCACAACGGCGGAGGC CGCCGGGTTCCCTGACGTGCCA GTCAGGCCTTCTCCTTTTCCGC AGACCGTGTGTTTCTTTACCGC TCTCCCCCGAGACCTTTTAAGG GTTGTTTGGAGTTTTAGATGCA AAATCCACAAGTATTCAAGTGA TTGTTAAAGAGGGAGGCCTGAA GTTGATTCAGATCCAAGACAAT GGCACCGGGATCAGG |

Example 2

As a result of the analysis of Example 1, it was found that 3 types of variants as the transcripts of the hMLH1 gene are present. The hMLH1 gene had previously been known as a gene associated with malignant transformation of cells. This time, the presence of transcriptional variants has been clarified for the first time, and thus, association of such variants with cancer has been anticipated.

Thus, focusing attention on variant types 1 and 3, the expression levels of such variants were measured by real-time PCR, and the expression level in cancer cell lines was compared.

As test materials, cultured cell lines LoVo, COLO320DM, COLO201, SW48, RKO, and HCT116 (all of which were cells derived from human colorectal cancer) were purchased from ATCC (American Type Culture Collection) and the Health Science Research Resources Bank, the Japan Health Sciences Foundation, and such cultured cell lines were then used. Each type of cells were cultured in an Advanced DMEM medium (Invitrogen) supplemented with 10% FBS (Invitrogen). Thereafter, total RNA was extracted from the cell lines using RNeasy Tissue Kit manufactured by QIAGEN. The extracted total RNA was used as a test sample in a reverse transcription and real-time PCR, as described later.

In addition, primers and probes used in the real-time PCR were designed. Such primers and probes were designed using Primer Express Software included with a real-time PCR apparatus, ABI PRISM 7900HT (Applied Biosystems). From the searching results of primers and probes obtained by inputting various conditions, the top 10 pairs having higher scores were selected. Using such 10 pairs, the real-time PCR was actually carried out for evaluation. As a result, good results were obtained from all of the 10 pairs. Thus, using the combination of primers and probes having the highest score, the following experiment was carried out.

SuperScript™ III Reverse Transcriptase (Invitrogen) was used in a reverse transcription (cDNA synthesis reaction). First, 2.0 μl of oligo(dT)$_{20}$primers (50 μM), 2.0 μg of total RNA, and 4.0 μl of dNTPs (5 mM) were added to a tube, and a DEPC-treated water was then added thereto, so as to prepare a mixture having a total volume of 26 μl. Subsequently, the mixture was incubated at 65° C. for 5 minutes, and it was then rapidly transferred onto ice. Thereafter, 5× First Strand Buffer (8.0 μl), 0.1 M DTT (2.0 μl), SuperScript™ III Reverse Transcriptase (2.0 μl), and a DEPC-treated water (2.0 μl) were added thereto, so as to prepare a mixture having a total volume of 40 μl. This mixture was vortexed, and it was then centrifuged, so as to collect a solution to the bottom of the tube, followed by incubation at 50° C. for 60 minutes. Thereafter, it was further incubated at 70° C. for 15 minutes, so as to terminate the reaction.

Subsequently, using the above obtained reverse transcript as a template, the real-time PCR was carried out employing ABI PRISM 7900HT (Applied Biosystems), so as to quantify each of variant type 1 and variant type 3 contained in the reverse transcript derived from each type of cells.

In order to amplify variant type 1 by PCR, 1.0 μl of a reverse transcript as template DNA, 10 μl of 1× Mastermix, 3.5 µl of a 5.0 µM sense primer (5'-CAGCGGCCAGCTAAT-GCTAT-3'; SEQ ID NO: 6), 3.5 µl of a 5.0 µM antisense primer (5'-CCATTGTCTTGGATCTGAATCAACTTC-3'; SEQ ID NO: 7), 5.0 µl of 5.0 µM TaqMan® probe (5'-CAAG-TATTCAAGTGATTGTTAAAGAGGGAGGCC-3'; SEQ ID NO: 9), and 1.0 µl of extra pure water were mixed, so as to prepare a reaction solution having a total volume of 20 µl. Likewise, in order to amplify variant type 3 by PCR, 1.0 µl of a reverse transcript as template DNA, 10 µl of 1× mastermix, 3.5 µl of a 5.0 µM sense primer (5'-GGGTTGTTTG-GAGTTTTAGATGCA-3'; SEQ ID NO: 8), 3.5 µl of a 5.0 µM antisense primer (5'-CCATTGTCTTGGATCTGAAT-CAACTTC-3'; SEQ ID NO: 7), 5.0 µl of 5.0 µM TaqMan® probe (5'-CAAGTATTCAAGTGATTGTTAAAGAGG-GAGGCC-3'; SEQ ID NO: 9), and 1.0 µl of extra pure water were mixed, so as to prepare a reaction solution having a total volume of 20 µl. It is to be noted that the TaqMan® probe used herein was capable of detecting both variant types 1 and 3. The above TaqMan® probe was manufactured by Applied Biosystems Japan Ltd. The 5'-terminus thereof was labeled with FAM (a fluorescent substance), and the 3'-terminus thereof was labeled with TAMRA (a quenching substance). The prepared reaction solution was subjected to a PCR using ABI PRISM 7900HT (Applied Biosystems), wherein after a reaction at 95° C. for 10 minutes, a reaction consisting of 95° C., 15 seconds, and 60° C., 1 minute, was repeated for 40 cycles. Thereafter, the fluorescence intensity was measured.

Moreover, in order to produce a calibration curve that is used to calculate the amount of DNA contained in the sample based on the fluorescence intensity measured in the real-time PCR, before carrying out the real-time PCR, a PCR product had previously been prepared from the aforementioned reverse transcript derived from the COLO320DM in the following process. First, in order to amplify variant type 1 by PCR, 2.0 µl of a reverse transcript as template DNA, 5.0 µl of a 10×PCR buffer, 4.0 µl of dNTP Mix (2.5 mM each), 3.5 µl of a 5.0 µM sense primer (5'-CTGGACGAGACAGTGGT-GAAC-3'; SEQ ID NO: 10), 3.5 µl of a 5.0 µM antisense primer (5'-ATACTGGCTAAATCCTCAAAGGACTG-3'; SEQ ID NO: 11), 0.25 µl of Ex Taq polymerase, and 37 µl of extra pure water were mixed, so as to prepare a reaction solution having a total volume of 50 µl. In order to amplify variant type 3 by PCR, a reaction solution was prepared with the same composition as that used in PCR amplification of the aforementioned variant type 1, with the exception that the sense primer was changed to that as shown in SEQ ID NO: 12 (5'-TTTCTTTACCGCTCTCCCCCG-3'). Each of the prepared reaction solutions was reacted at 95° C. for 10 minutes, and thereafter, a reaction consisting of 95° C., 30 seconds, 63° C., 1 minute, and 72° C., 1 minute, was repeated for 35 cycles. Finally, a reaction at 72° C. for 10 minutes was carried out. With regard to the thus obtained PCR product derived from the COLO320DM, the amount of DNA thereof was measured, and it was then subjected to serial dilution. Using the resultant as template DNA, the same amplification as for other reverse transcripts was carried out in the aforementioned real-time PCR. Thereafter, the fluorescence intensity was measured as described above, and a calibration curve was then produced based on the obtained value according to a routine method.

From the Ct (Threshold Cycle) value obtained from the fluorescence intensity measured as described above and the above produced calibration curve, the amounts of variant types 1 and 3 contained in an initial transcript contained in total RNA extracted from each cell were calculated. The measurement values of the amounts of variant types 1 and 3 correspond to their expression levels, respectively.

Figures 2A, 2B:
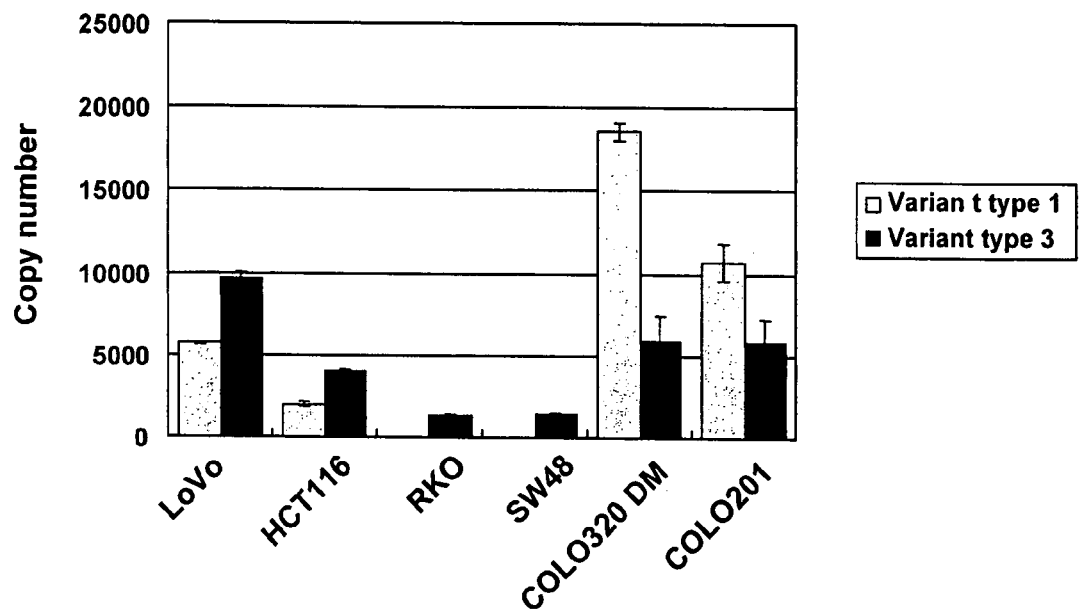
FIG. 2A shows the expression levels of transcriptional variant types 1 and 3 of the hMLH1 genes in 6 types of cancer cell lines. The filled bar indicates variant type 1, and the open bar indicates variant type 3.
FIG. 2B shows a result of making a comparison between the expression levels of variant type 1 and of variant type 3 in each cancer cell line as shown in the graph in FIG. 2A.

The results obtained by quantifying the expression levels of variant types 1 and 3 in 6 types of colorectal cancer cell lines, as described above, are shown in FIG. 2. As shown in FIG. 2, the expression of variant type 1 was detected in LoVo, HCT116, COLO320DM, and COLO201. However, the expression thereof was not detected in RKO and SW48 (less than detection limit). These results correspond to the previous report (Non-Patent Document 5). On the other hand, the expression pattern of variant type 3, the existence of which had been discovered by the present inventors, clearly differed from the expression pattern of variant type 1. The expression of variant type 3 was detected in RKO or SW48, in which the expression of variant type 1 that was hMLH1 had not been detected in the previous report. Further, it was also shown that the expression level of variant type 3 was significantly higher than that of variant type 1 in LoVo and HCT116. Such results were contrary to the prediction in the analysis of Example 1 that variant type 1 was a major transcript of the hMLH1 gene and that the expression level of variant type 3 was low. Thus, LoVo and HCT116 in which the expression level of variant type 3 was higher than that of variant type 1, and RKO and SW48 in which variant type 3 was detected but variant type 1 was not detected, were microsatellite instability (MSI) positive whose information was obtained from Non-Patent Document 5 (FIG. 2; Non-Patent Document 5). Furthermore, the degree of methylation of the promoter region of the hMLH1 gene, which has an influence upon the expression level of the above gene, was examined based on the descriptions of Non-Patent Document 5. As a result, it was found that methylation of the promoter region of the hMLH1 gene was detected only in RKO and SW48, in which variant type 3 had been detected but variant type 1 had not been detected. That is, it was considered that such methylation of the promoter region of the hMLH1 gene suppresses the expression of variant type 1, but that it does not suppress the expression of variant type 3.

Taking into consideration the facts that the hMLH1 gene has been known to be associated with hereditary non-polyposis colorectal cancer (HNPCC), and that it has been known that microsatellite instability becomes positive with high frequency in various types of cancers including HNPCC, it is considered that a relative increase in the expression level of variant type 3 compared to the transcriptional variant type 1 of the hMLH1 gene is in correlation with MSI positive in cancer and methylation of a promoter region.

The conditions for expression of variant type 3 and the specific actions of the expression itself on the occurrence of cancer still remain unknown. There may be a possibility that the transcriptional variant type 3 itself could not affect MSI, and thus the occurrence of cancer, but that a decrease in the expression level of variant type 1 or the loss thereof could become a major factor for inducing MSI. However, in spite of estimation of such mechanisms, when compared with the transcriptional variant type 1, if the expression level of variant type 3 was relatively increased, it was clear that there was the presence of cancer cells associated with MSI.

INDUSTRIAL APPLICABILITY

The detection method of the present invention enables simple and clear detection of the presence of a cancer cell such as colorectal cancer in a cancer sample even at an extremely early stage. The detection results obtained by the present method are useful in diagnosing cancer with microsatellite instability, such as HNPCC, at an early stage.

SEQUENCE LISTING FREE TEXT

SEQ ID NOS: 6 to 8 and 10 to 12 represent primers.

SEQ ID NO: 9 represents a probe.

What is claimed is:

1. A method for detecting the possible presence of microsatellite instability in a biological sample comprising:
(i) measuring, in the biological sample, the mRNA expression level of a first transcript of a human MLH1 gene containing the nucleotide sequence of SEQ ID NO: 1 at the 5'-terminus thereof and the mRNA expression level of a second transcript of a human MLH1 gene containing the nucleotide sequence of SEQ ID NO: 2 at the 5'-terminus thereof using a primer pair (a) and a primer pair (b), wherein the primer pair (a) is a combination of a primer comprising the nucleotide sequence as shown in SEQ ID NO: 6 with a primer comprising the nucleotide sequence of SEQ ID NO: 7, and wherein the primer pair (b) is a combination of a primer comprising the nucleotide sequence as shown in SEQ ID NO: 8 with a primer comprising the nucleotide sequence of SEQ ID NO: 7, and wherein the expression levels are measured using a real-time PCR method; and
(ii) comparing the expression levels measured in (i), wherein a mRNA expression level of the second transcript that is higher than the mRNA expression level of the first transcript indicates the possible presence of microsatellite instability.

2. The method according to claim 1, wherein said real-time PCR method comprises the use of an oligonucleotide probe labeled with a fluorescent substance and a quenching substance.

3. The method according to claim 1, wherein a probe comprising the nucleotide sequence as shown in SEQ ID NO: 9, to one end of which a fluorescent substance is added and to the other end of which a quenching substance is added, is used in the real-time PCR method.

* * * * *